United States Patent [19]

Washizuka

[11] Patent Number: 4,911,147
[45] Date of Patent: Mar. 27, 1990

[54] ENDOSCOPE WITH A SHOCK ABSORBER

[75] Inventor: Nobuhiko Washizuka, Tokyo, Japan

[73] Assignee: Olympus Optical Co., Ltd., Tokyo, Japan

[21] Appl. No.: 311,455

[22] Filed: Feb. 16, 1989

[30] Foreign Application Priority Data

Apr. 28, 1988 [JP] Japan .............................. 63-105674

[51] Int. Cl.⁴ .............................................. A61B 1/00
[52] U.S. Cl. ...................................................... 128/6
[58] Field of Search ......................... 128/4, 6; 358/98

[56] References Cited

U.S. PATENT DOCUMENTS

| | | | |
|---|---|---|---|
| 3,903,877 | 9/1975 | Terada ................................. | 128/6 |
| 4,281,646 | 8/1981 | Kinoshita ............................ | 128/6 |
| 4,361,139 | 11/1982 | Takagi ................................. | 128/6 |
| 4,667,655 | 5/1987 | Ogiu et al. .......................... | 128/6 |
| 4,676,592 | 6/1987 | Nishioka et al. ................... | 128/4 |
| 4,677,471 | 6/1987 | Takamura et al. ................. | 128/6 |

FOREIGN PATENT DOCUMENTS 2426771 12/1974 Fed. Rep. of Germany .
59-141305 9/1984 Japan .

Primary Examiner—William H. Grieb
Attorney, Agent, or Firm—Kenyon & Kenyon

[57] ABSTRACT

An endoscope provided with an elastic member between an optical lens and the distal end portion of an inserting portion of the endoscope, the optical lens being fixed to the distal end portion via the elastic member. Shock waves for crushing a calculus transmitted to the optical lens can be absorbed by the elastic member.

22 Claims, 4 Drawing Sheets

ENDOSCOPE WITH A SHOCK ABSORBER

BACKGROUND OF THE INVENTION

1. Field of the Invention

This invention relates to an endoscope provided with an optical lens at the distal end of an inserting portion.

2. Description of Related Art

Generally, an endoscope comprises an operating portion and an inserting portion, and a lens frame holding an optical lens such as an objective is provided at the distal end of the inserting portion.

Conventionally, the optical lens has been directly bonded to the lens frame, as disclosed in Laid-Open Japanese Utility Model Application, Publication No. 59-141305.

In recent years, electrohydraulic calculus crushing apparatus have been used with endoscopes to crush calculi formed in kidneys, urethrae, biliary tracts, etc. The electrohydraulic calculus crushing apparatus comprises a power source unit and a flexible probe having electrodes at its tip. The probe is inserted in a channel of an endoscope, and the tip of the probe is protruded to approach the aimed calculus while one observes through the endoscope. When electricity is discharged between the electrodes provided at its tip, shock waves are produced to crush the calculus.

In this case, however, the shock waves produced between the electrodes at the tip of the probe affect the distal end portion of the endoscope. In a conventional endoscope in which the optical lens is directly bonded to the lens frame, the shock waves are transmitted to the optical lens without being absorbed. Thus, if a plurality of optical lenses are fixed to the lens frame and spaced from each other for focus adjustment, the bonding of the front optical lens may be loosened by the pressure of the shock waves, and the front optical lens may clash against an inner optical lens so that the lenses may be cracked. Even if a single optical lens is bonded to the lens frame, the pressure of the shock waves will be concentrated on a surface to which the optical lens is bonded, and the optical lens may be cracked from that portion. Further, the bonding agent between the optical lens and the lens frame may come off owing to the shock waves, and water may enter the lens frame so that waterdrops may remain on the lens or the water may also reach an optical fiber bundle located on the inner side of the optical lens to affect the optical fibers.

SUMMARY OF THE INVENTION

An object of the present invention is to provide an endoscope wherein an optical lens supported in the distal end portion of the endoscope is neither cracked nor comes off from a lens frame owing to shock waves even if the endoscope is used for crushing calculi formed in kidneys, urethrae, biliary tracts, etc. by means of the shock waves.

In order to attain the above object, an endoscope according to the present invention is provided with an elastic member between an optical lens and the distal end portion of an inserting portion of the endoscope, and the optical lens is fixed to the distal end portion via the elastic member. The shock waves for crushing a calculus transmitted to the optical lens can be absorbed by the elastic member.

DESCRIPTION OF THE PREFERRED EMBODIMENTS

Figure 1:
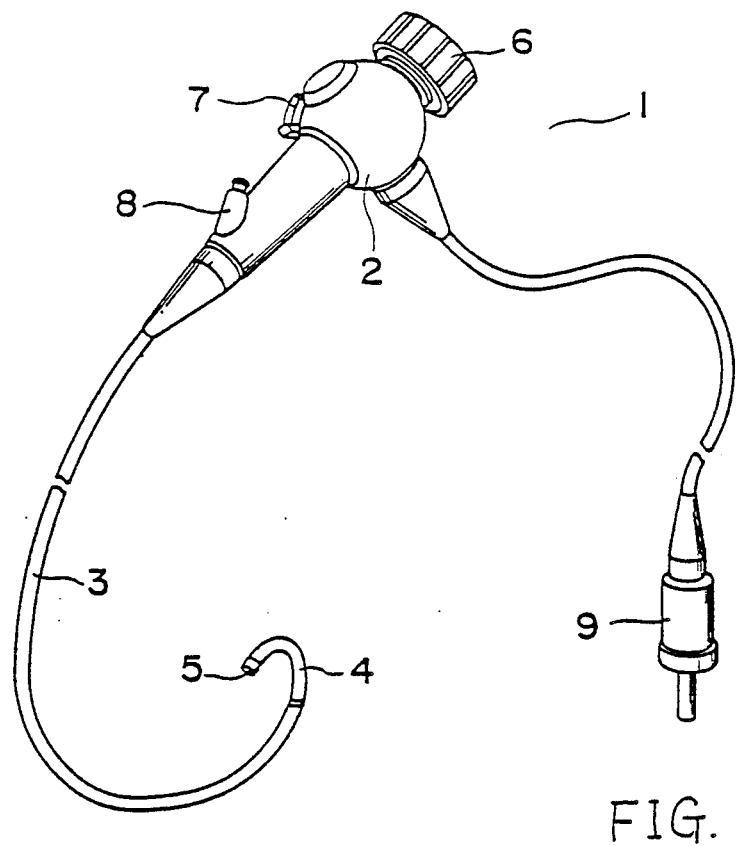
FIG. 1 is an external view of an endoscope according to a first embodiment of the present invention.
Figure 2:
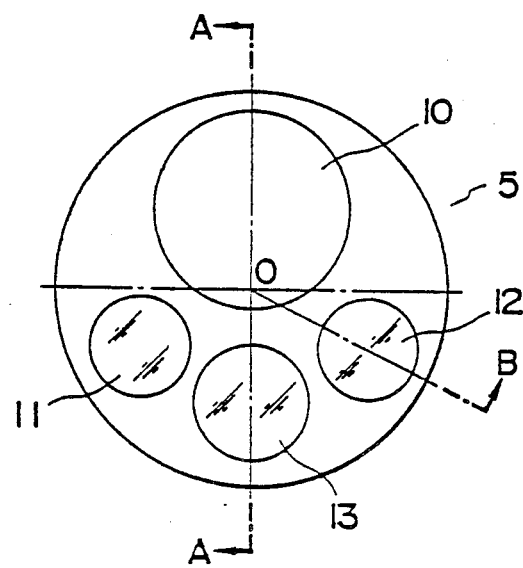
FIG. 2 is a front view of the distal end portion of an inserting portion of the endoscope shown in FIG. 1.
Figure 3:
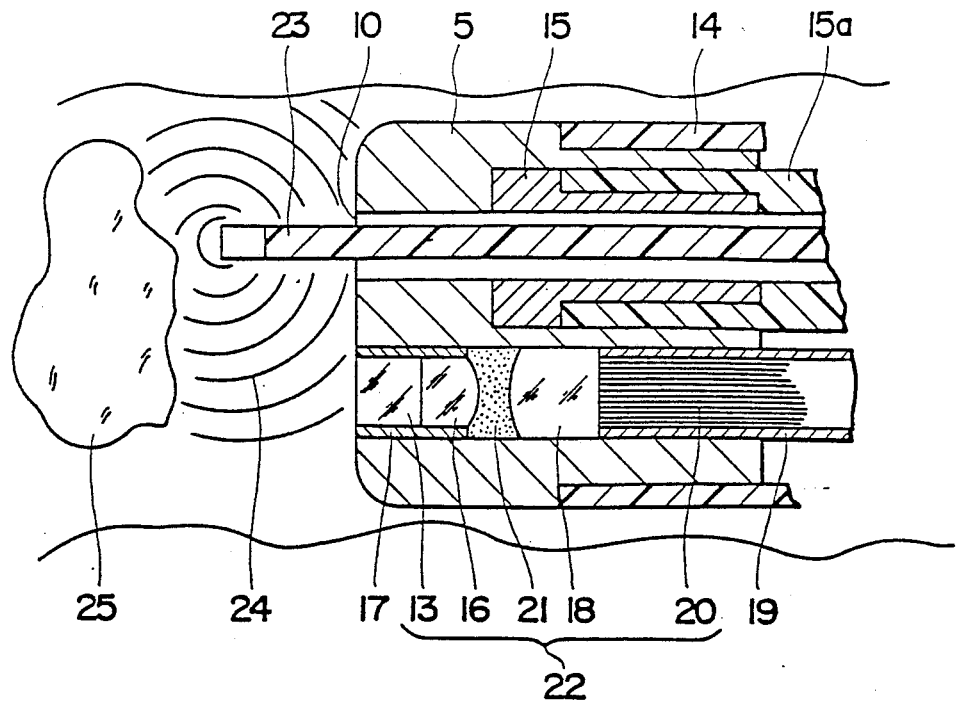
FIG. 3 is a partial sectional view of the distal end portion taken on line A—A of FIG. 2.

Referring to FIGS. 1 to 3, a first embodiment of the present invention is described.

FIG. 1 is an external view of an endoscope 1 having an operating portion 2, an inserting portion 3, a bending portion 4, and a tip frame 5 provided at the distal end of the bending portion 4. The operating portion 2 is provided with an eyepiece portion 6, a bending lever 7 for bending the bending portion 4, and a channel mouthpiece 8 communicating with a channel (not shown) provided in the inserting portion 3. The operating portion 2 is coupled through a cord to a connector 9 to be connected with a light source unit (not shown).

FIG. 2 is a front view of the distal end portion of the inserting potion of the endoscope 1. The tip frame 5 is provided with a channel opening 10 communicating with the channel mouthpiece 8; illuminating lenses 11 and 12 for emitting illumination light transmitted through light guide fibers; and a cover glass 13 arranged in front of an objective.

FIG. 3 is a partial sectional view taken on line A—A of FIG. 2 and shows a main part of the present invention. The tip frame 5 is bonded to an outer tube 14. Communicating with the channel opening 10, a channel tube 15a with a mouthpiece 15 is bonded to the tip frame 5. The cover glass 13 is bonded to the front plane surface of a first objective 16 and fixed to a lens frame 17. The lens frame 17 is not bonded to the tip frame 5. A second objective 18 is arranged behind the first objective 16, and the rear plane surface of the second objective 18 is bonded to an end surface of image guide fibers 20 having a mouthpiece 19. By bonding the mouthpiece 19 to the tip frame 5, the second objective 18 and the image guide fibers 20 are integrally fixed to the tip frame 5. An elastic member 21 made of a transparent material is arranged between, and bonded to, the first and second objectives 16 and 18. Thus a viewing optical system 22 as illustrated is formed in such a manner that the lens frame 17 to which the cover glass 13 and the first objective 16 are bonded, the transparent elastic member 21, the second objective 18, and the image guide 20 are bonded to each other in this order with the mouthpiece 19 of the image guide 20 being bonded to the tip frame 5.

When the endoscope 1 having the viewing optical system 22 as described above is used to crush a calculus 25 with a probe 23 of an electrohydraulic calculus crushing apparatus as shown in FIG. 3, the endoscope 1 is inserted in the vicinity of the calculus 25 while one is viewing through the eyepiece portion 6. Then the probe 23 for producing shock waves to crush a calculus is inserted into the channel of the endoscope 1 through the channel mouthpiece 8, and the tip of the probe 23 is protruded to approach the aimed calculus 25. When the tip of the probe 23 is positioned in the vicinity of the calculus 25, shock waves 24 are produced from the tip of the probe 23 by electrical discharge. The shock waves 24 are transmitted to the distal end of the endoscope 1 as well as to the calculus 25 to crush it. The shock waves impinge on the cover glass 13 to cause the lens frame 17 containing the first objective 16 to vibrate. However, the vibration of the lens frame 17 is absorbed by the elastic member 21.

That is, since the lens frame 17 holding the first objective 16 is not directly fixed to the tip frame 5, but is fixed thereto together with the second objective 18 via the elastic member 21 to absorb the shock waves, the shock waves will not cause the objectives to clash with each other to crack. Further, since the elastic member arranged between the objectives absorbs the shock waves, the adhesive can be prevented from coming off, thus water will not enter the inside of the tip frame.

Moreover, if a transparent elastic coating material is applied to the front surface of the cover glass 13, the shock can be absorbed more effectively.

Next, referring to FIGS. 4 to 8, other embodiments of the present invention will be described. The same elements as those of the first embodiment are assigned the same numerals and their description is omitted.

Figure 4:
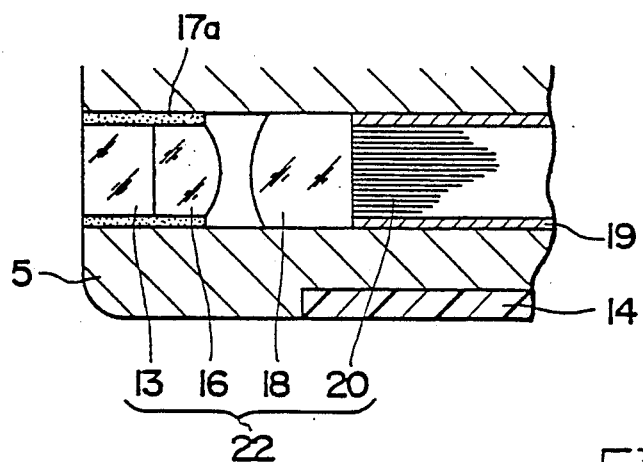
FIG. 4 is a partial sectional view of a viewing optical system of an endoscope according to a second embodiment of the present invention.

FIG. 4 shows a viewing optical system 22 of a second embodiment of the invention. A lens frame 17a fixedly holding the same cover glass 13 and first objective 16 as shown in FIG. 3 of the first embodiment is formed by an elastic member and fixed to a tip frame 5. The elastic member 21 of FIG. 3 arranged between the objectives has been removed.

In this embodiment, since the lens frame 17a formed by an elastic member can absorb the vibration of the shock waves 24 transmitted to the cover glass 13, the clash of the objectives and the coming off of the adhesive can be prevented.

Figure 5:
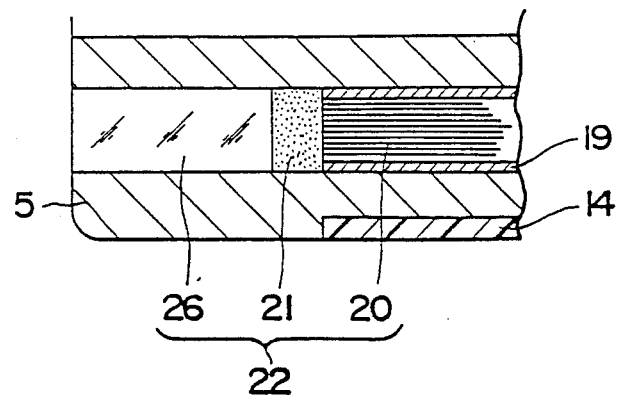
FIG. 5 is a partial sectional view of a viewing optical system of an endoscope according to a third embodiment of the present invention.

FIG. 5 illustrates a third embodiment in which a viewing optical system 22 is formed by a rod-shaped optical lens 26 and image guide fibers 20. A mouthpiece 19 of the image guide fibers 20 is bonded to a tip frame 5. The end surface of the image guide fibers 20 is bonded to a cylindrical transparent elastic member 21, the other end of which is bonded to he rod-shaped optical lens 26. The rod-shaped optical lens 26 is not bonded to the tip frame 5.

Also in this embodiment, even if the shock waves 24 are transmitted to the optical lens 26 to vibrate it, this vibration can be absorbed by the elastic member 21.

Figure 6:
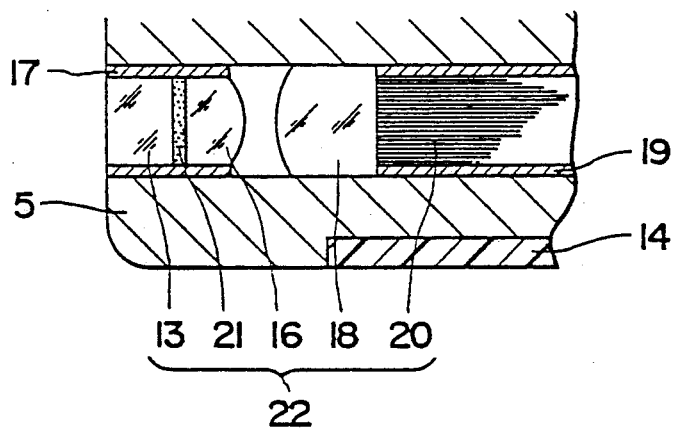
FIG. 6 is a partial sectional view of a viewing optical system of an endoscope according to a fourth embodiment of the present invention.

In FIG. 6, a fourth embodiment of the present invention is illustrated. An elastic member 21 is arranged between a cover glass 13 and a first objective 16 held by a lens frame 17 of a viewing optical system 22. The lens frame 17 is fixed to a tip frame 5, and the first objective 16 is bonded to the lens frame 17. The elastic member 21 is bonded to the first objective 16, and the cover glass 13 is bonded to the elastic member 21. The cover glass 13 is not bonded to the lens frame 17.

In this embodiment, the impulsive force applied to the cover glass 13 can be absorbed by the elastic member 21 arranged in the lens frame 17.

The above embodiments relate to optical lenses used in viewing optical systems. Now, other embodiments of the present invention relating to illuminating optical systems will be described.

Figure 7:
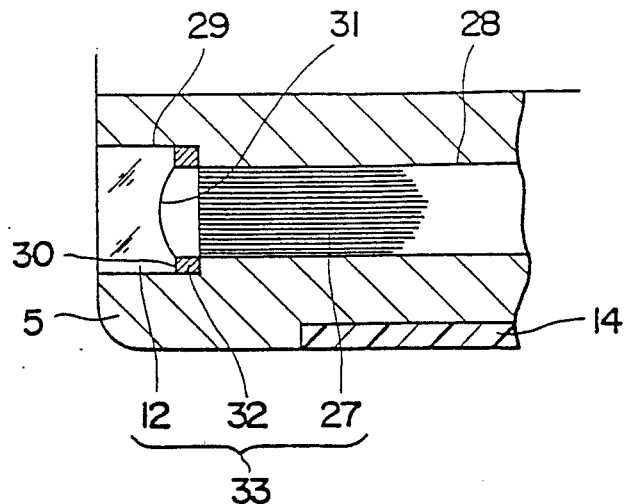
FIG. 7 is a partial sectional view of an illuminating optical system of an endoscope according to a fifth embodiment of the present invention.

FIG. 7 is a partial sectional view taken on line 0-B of FIG. 2 and shows a fifth embodiment of the present invention. A tip frame 5 is provided with a first receiving portion 28 for receiving and fixing light guide fibers 27, and the light guide fibers 27 are inserted and fixed in the first receiving portion 28. The tip frame 5 is also provided with a second receiving portion 29 for receiving an illuminating lens 12, and the illuminating lens 12 is received therein. One side of the illuminating lens 12 is plane and the other side has a plane portion 30 and a concave portion 31. The plane portion 30 is bonded to an annular elastic member 22 fixed to the tip frame 5. The illuminating lens 12 is not directly bonded to the tip frame 5. These elements constitute an illuminating optical system 33.

In this embodiment, although the illuminating lens 12 is vibrated by the pressure of the shock waves 24, the annular elastic member 32 absorbs the vibration to prevent the illuminating lens 12 from being cracked.

Figure 8:
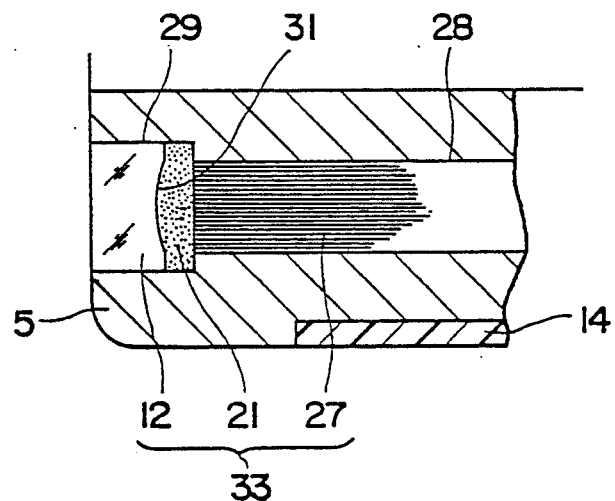
FIG. 8 is a partial sectional view of an illuminating optical system of an endoscope according to a sixth embodiment of the present invention.

FIG. 8 illustrates a sixth embodiment of the present invention. A transparent elastic member 21 is arranged between an end surface of light guide fibers 27 and an illuminating lens 12. The elastic member 21 is fixed to a tip frame 5 in a second receiving portion 29 and bonded to the illuminating lens 12.

Also in this embodiment, the impulsive force applied to the illuminating lens 12 can be absorbed by the elastic member 21.

According to the present invention, as described above, an endoscope with an optical lens exposed to the outside in the distal end portion of the endoscope is provided with an elastic member between the optical lens and the distal end portion, and the optical lens is fixed to the distal end portion via the elastic member. Therefore, if shock waves are used for crushing a calculus and the optical lens is vibrated due to the pressure of the shock waves, the elastic member absorbs the vibration so that the optical lens can be prevented from being cracked due to the shock waves and the adhesive bonding of the optical lens can be protected from being loosened.

In the above-described embodiments, the objective is a rigid lens, and a separate elastic member is provided. However, the same effect can be obtained if the objective itself is formed by a transparent elastic material.

What is claimed is:

1. An endoscope comprising:
   an inserting portion having a distal end;
   a tip fixed to the distal end of the inserting portion;
   an optical member fitted in and supported by the tip; and
   fixing means for fixing the optical member to the tip elastically in such a manner that the optical member is slidable in the axial direction of the tip.

2. The endoscope of claim 1, wherein the fixing means comprises a frame for supporting the optical member rigidly; and an elastic member directly or indirectly fixed to the optical member and the tip .

3. The endoscope of claim 1 or 2 further comprising a viewing optical system including an objective, the optical member being a cover glass provided in front of the objective.

4. The endoscope of claim 1, wherein the fixing means is an elastic frame fixed to the tip and the optical member.

5. The endoscope of claim 1, wherein the optical member is a rod-shaped optical lens.

6. The endoscope of claim 1, wherein the fixing means is made of a transparent elastic material and arranged next to the optical member.

7. The endoscope of claim 1, wherein the fixing means is a ring-shaped elastic member fixed to the tip and the optical member.

8. An endoscope for use with an electrohydraulic calculus crushing apparatus having a probe, the endoscope comprising:
   an inserting portion having a distal end, the distal end having an opening through which the probe of the electrohydraulic calculus crushing apparatus can be exposed;
   an optical system disposed in the distal end of the inserting portion and having at least one cover means exposed at the distal end; and
   an elastic member disposed between the cover means and the distal end of the inserting portion for indirectly fixing the cover means to the distal end elastically.

9. The endoscope of claim 8, wherein the optical system comprises an objective, and the cover means comprises a cover glass mounted in front of the objective to protect the objective from external force, and a frame for supporting the cover glass.

10. The endoscope of claim 8, wherein the optical system comprises two objectives, and the elastic member is transparent and arranged between the two objectives.

11. An endoscope comprising:
   an inserting portion having a distal end;
   a tip connected to the distal end of the inserting portion and having an opening provided through the tip;
   an optical member disposed in the opening of the tip; and
   supporting means for elastically supporting the optical member to allow the optical member to move axially thereby to prevent the vibration of the optical member from being transmitted to the tip.

12. The endoscope of claim 11, wherein the optical member comprises a ring frame fitted in the opening of the tip.

13. The endoscope of claim 11, wherein the optical member is supported in the opening of the tip slidably in its axial direction, the supporting means is formed by an elastic ring which is positioned to contact the optical member at its periphery, and the tip has a surface for supporting the ring.

14. An endoscope for use with an electrohydraulic calculus crushing apparatus, the endoscope comprising:
   an inserting portion having a distal end;
   a tip provided at the distal end of the inserting portion and having a front surface and a cylindrical hole extending in the axial direction of the tip; and
   an optical system fitted in the cylindrical hole and including a first optical element exposed to the outside at the front surface of the tip, the optical element being supported in the cylindrical hole slidably only in the axial direction of the tip.

15. The endoscope of claim 15, wherein the optical system includes a second optical element adjacent to the first optical element and fixed in the cylindrical hole, and the first and second optical elements are coupled to each other via an elastic member.

16. The endoscope of claim 16, wherein the elastic member is made of a transparent elastic material.

17. The endoscope of claim 15, wherein the optical system includes a light guide for transmitting illumination light, the cylindrical hole has a relatively small diameter portion for receiving the light guide and a relatively large diameter portion for receiving the first optical element with a step portion formed between the relatively small diameter portion and the relatively large diameter portion, and an elastic member is interposed between the first optical member and the step portion to support the first optical member slidably in the axial direction of the tip.

18. The endoscope of claim 18, wherein the elastic member is annular and has a central hole for allowing illumination light to pass through.

19. The endoscope of claim 18, wherein the elastic member has such a form as to fill the space between the first optical member and the step portion and is made of a transparent elastic material.

20. An endoscope for use with an electrohydraulic calculus crushing apparatus, the endoscope including an inserting portion having a distal end, the electrohydraulic calculus crushing apparatus having an operating portion which is to be protruded from the distal end of the inserting portion to crush a calculus, the endoscope comprising:
   a tip portion at the distal end of the inserting portion and having a front surface and a cylindrical hole extending in the axial direction of the tip;
   a tubular sliding member provided in the cylindrical hole slidably in the axial direction of the tip;
   elastically supporting means for supporting the sliding member elastically in the axial direction of the tip; and
   an optical element fixedly supported by the sliding member and exposed to the outside at the front surface of the tip.

21. The endoscope of claim 21, wherein the elastically supporting means is an elastic member interposed between the sliding member and a fixed member adjacent to the sliding member in the axial direction of the tip.

22. An endoscope for use with an electrohydraulic calculus crushing apparatus, the endoscope including an inserting portion having a distal end, the electrohydraulic calculus crushing apparatus having an operating portion which is to be protruded from the distal end of the inserting portion to crush a calculus, the endoscope comprising:
   a tip provided at the distal end of the inserting portion and having a receiving space extending in the axial direction of the tip; and
   a viewing optical system arranged in the receiving space and having a front optical element group and a rear optical element group, the front optical element group being elastically supported to be slidable in the axial direction of the tip, and the rear optical element group being fixed in the receiving space.

* * * * *

UNITED STATES PATENT AND TRADEMARK OFFICE
CERTIFICATE OF CORRECTION

PATENT NO. : 4,911,147

DATED : March 27, 1990

INVENTOR(S) : Nobuhiko WASHIZUKA

It is certified that error appears in the above-identified patent and that said Letters Patent is hereby corrected as shown below:

Column 1, line 66, change "The shock waves" to --Thus shock waves--.

Column 2, line 41, change "potion" to --portion--.

Column 3, line 56, change "he rod-shaped" to --the rod-shaped--.

Column 4, line 21, change "22" to --32--.

Column 6, lines 3 and 10, change "claim 15" to --claim 14--.

Column 6, line 8, change "claim 16" to --claim 15--.

Column 6, lines 21 and 24, change "claim 18" to --claim 17--.

UNITED STATES PATENT AND TRADEMARK OFFICE
CERTIFICATE OF CORRECTION

PATENT NO. : 4,911,147
DATED : March 27, 1990
INVENTOR(S) : Nobuhiko WASHIZUKA

It is certified that error appears in the above-identified patent and that said Letters Patent is hereby corrected as shown below:

Column 6, line 35, change "a tip portion" to --a tip provided--.

Column 6, line 46, change "claim 21" to --claim 20--.

Signed and Sealed this

Thirtieth Day of July, 1991

Attest:

HARRY F. MANBECK, JR.

Attesting Officer

Commissioner of Patents and Trademarks